United States Patent [19]

Yim et al.

[11] Patent Number: 5,385,887
[45] Date of Patent: Jan. 31, 1995

[54] FORMULATIONS FOR DELIVERY OF OSTEOGENIC PROTEINS

[75] Inventors: Kalvin W. K. Yim, N. andover; Michael C. Huberty, Andover; Richard P. Northey, Jr., Ipswich; Jay A. Schrier, Andover, all of Mass.

[73] Assignee: Genetics Institute, Inc., Cambridge, Mass.

[21] Appl. No.: 119,772

[22] Filed: Sep. 10, 1993

[51] Int. Cl.$^6$ ........................ A61K 37/02; C07K 13/00
[52] U.S. Cl. ........................................ 514/12; 530/350;
530/397; 530/399; 530/840; 514/8; 514/21;
424/423; 424/426; 106/645
[58] Field of Search ............... 106/645, 646, 650, 651,
106/652, 653; 424/78.08, 78.37, 422, 423, 424,
425, 426, 529; 514/8, 12, 21; 530/350, 397, 399,
840; 623/11, 16, 17, 18, 19, 20, 21, 22, 23

[56] References Cited

U.S. PATENT DOCUMENTS 5,013,649  5/1991  Wang et al. .................. 435/69.1
5,171,579  12/1992  Ron et al. ..................... 424/486

FOREIGN PATENT DOCUMENTS 2093348  9/1982  United Kingdom .......... 424/426
8404674  12/1984  WIPO ............................ 424/423

Primary Examiner—Michael G. Wityshyn
Assistant Examiner—Nancy J. Gromet
Attorney, Agent, or Firm—Steven R. Lazar; Thomas J. DesRosier

[57] ABSTRACT

A composition is disclosed comprising a pharmaceutically acceptable admixture of an osteogenic protein; a porous particulate polymer matrix; an osteogenic protein-sequestering amount of blood clot; and a calcium sulfate hemihydrate-containing substance. Also disclosed are formulations of bone morphogenetic proteins with improved solubility and/or stability characteristics.

7 Claims, No Drawings

FORMULATIONS FOR DELIVERY OF OSTEOGENIC PROTEINS

BACKGROUND OF THE INVENTION

The subject invention relates to the field of osteogenic proteins and pharmaceutical formulations thereof. More particularly, the subject invention involves pharmaceutical formulations designed to sequester osteogenic protein in situ for a time sufficient to allow the protein to induce cartilage and/or bone formation.

Osteogenic proteins are those proteins capable of inducing, or assisting in the induction of, cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. No. 4,877,864 and Wang et al. U.S. Pat. No. 5,013,549); a family of transforming growth factors (TGF-$\alpha$ and TGF-$\beta$) has been identified as potentially useful in the treatment of bone disease (see e.g. Derynck et al., EP 154,434); a protein designated Vgr-1 has been found to be expressed at high levels in osteogenic cells (see Lyons et al. (1989) Proc. Nat'l. Acad. Sci. USA 86, 4554–4558); and proteins designated OP-1, COP-5 and COP-7 have purportedly shown bone inductive activity (see oppermann, et al. U.S. Pat. No. 5,001,691).

Various attempts have been made at developing formulations designed to deliver osteogenic proteins to a site where induction of bone formation is desired. For example, certain polymeric matrices such as acrylic ester polymer (Urist, U.S. Pat. No. 4,526,909) and lactic acid polymer (Urist, U.S. Pat. No. 4,563,489) have been utilized, but these formulations do not sequester the osteogenic protein for a time sufficient to optimally induce bone formation, and further have been found to erode too slowly for optimal bone formation.

A biodegradable matrix of porous particles for delivery of an osteogenic protein designated as OP is disclosed in Kuberasampath, U.S. Pat. No. 5,108,753. While U.S. Pat. No. 5,108,753 discloses that a successful carrier for OP must bind the protein, act as a slow release delivery system, accommodate each step of the cellular response during bone development, and protect the protein from nonspecific proteolysis, no formulations are suggested which contain components that specifically sequester the OP at the site where bone formation is desired.

Ron et al., U.S. Pat. No. 5,171,579 discloses that the average surface area per porous particle is critical to optimize bone formation.

Okada et al., U.S. Pat. No. 4,652,441, U.S. Pat. No. 4,711,782, U.S. Pat. No. 4,917,893 and U.S. Pat. No. 5,061,492 and Yamamoto et al., U.S. Pat. No. 4,954,298 disclose a prolonged-release microcapsule comprising a polypeptide drug and a drug-retaining substance encapsulated in an inner aqueous layer surrounded by a polymer wall substance in an outer oil layer. Although bone morphogenic protein is listed as a polypeptide capable of such a formation, microencapsulation of osteogenic proteins prevents controlled release of such protein sufficient for optimal bone formation.

Yamazaki et al., Clin. Orthop. and Related Research, 234:240–249 (1988) disclose the use of implants comprising 1 mg of bone morphogenetic protein purified from bone and 5 mg of Plaster of Paris. U.S. Pat. No. 4,645,503 discloses composites of hydroxyapatite and Plaster of Paris as bone implant materials.

Collagen matrices have also been used as delivery vehicles for osteogenic proteins (see e.g. Jeffries, U.S. Pat. No. 4,394,370), but collagen frequently causes undesirable antigenic reactions in patients. Therefore, there remains a need for a pharmaceutical formulation capable of sequestering osteogenic proteins at a site where induction of bone formation is desired for a time sufficient to allow safe, effective induction of such bone formation.

SUMMARY OF THE INVENTION

The subject invention provides a composition comprising a pharmaceutically acceptable admixture of an osteogenic protein; a porous particulate polymer matrix, an osteogenic protein-sequestering amount of autogenous blood, and an acceptable quantity of a calcium sulfate hemihydrate-containing substance (CSHS). In another embodiment, the present invention comprises a pharmaceutically acceptable mixture of an osteogenic protein; an osteogenic protein-sequestering amount of autogenous blood, and an acceptable quantity of a CSHS. Yet another embodiment of the present invention comprises formulation of osteogenic protein and a suitable quantity of a CSHS. The formulations may optionally include other protein sequestering agents, particularly cellulosic materials.

Applicant has further found, surprisingly, that an improved formulation of BMPs, particularly BMP-2, which has improved solubility and stability characteristics, can be achieved using a composition of glycine, sucrose, and glutamic acid hydrochloride, at a pH of less than 6.0. In a preferred embodiment of the invention, this formulation comprises about 2.5% glycine (g/100 ml (w/v)), about 0.5% sucrose (w/v), about 5 mM glutamic acid hydrochloride (about 0.1% w/v), and about 0.01% (w/v) polysorbate 80, at a pH of about 4.5.

The compositions of the present invention are useful for the preparation of formulations of osteoinductive proteins which can be used, among other uses, to promote the formation of cartilage and/or bone, for repair of tissue damage and fractures.

DETAILED DESCRIPTION OF THE INVENTION

In U.S. Pat. No. 5,171,579, it is disclosed that osteogenic proteins can be sequestered at a site where bone inducing activity is desired using autogenous blood, without using antifibrinolytic agents, provided that a porous particulate polymer matrix is incorporated into the formulation. To reduce the preparation time and improve the above formulation's handling characteristics, Applicants have surprisingly found that it is desirable to add a calcium sulfate hemihydrate-containing substance (CSHS). The CSHS is preferably either pure calcium sulfate hemihydrate ($CaSO_4 \cdot \frac{1}{2}H_2O$), also known as Plaster of Paris (POP), or a mixture of POP and hydroxyapatite (POP:HA). Adding a CSHS reduces setup time and provides improved moldability and consistency of the resulting formulation.

The osteogenic proteins useful in the practice of the subject invention are well known to those skilled in the art and include those discussed above. The preferred osteogenic proteins for use herein are those of the BMP class identified as BMP-1 through BMP-10 in U.S. Pat. No. 4,877,864; U.S. Pat. No. 5,013,649; WO 90/11366 published Oct. 4, 1990; WO 91/18098 published Nov. 28, 1991; WO 93/00432, published Jan. 7, 1993 and U.S. Ser. No. 08/061,695, filed May 12, 1993. The disclosure of the above publications are hereby incorporated by reference. The most preferred is BMP-2, the full length cDNA sequence of which is described in detail in the '649 patent. Of course, combinations of two or more of such osteogenic proteins may be used, as may fragments of such proteins that also exhibit osteogenic activity. Such osteogenic proteins are known to be homodimeric species, but also exhibit activity as mixed heterodimers. Heterodimeric forms of osteogenic proteins may also be used in the practice of the subject invention. BMP heterodimers are described in WO93/09229, the disclosure of which is hereby incorporated by reference. Recombinant proteins are preferred over naturally occurring isolated proteins. The amount of osteogenic protein useful herein is that amount effective to stimulate increased osteogenic activity of infiltrating progenitor cells, and will depend upon the size and nature of defect being treated as discussed in more detail below, such amounts being orders of magnitude less than the amount of porous particulate polymer matrix employed, generally in the range of 1–50 μg of protein for each 10 mg of porous particulate polymer matrix employed and more preferably in the range of 0.5–10 μg protein for each milligram of polymer matrix employed (assuming 0.2 g/cc density).

The osteogenic proteins can be utilized in the form of a pharmaceutically acceptable solution (including reconstitution from a lyophilized form). It is optimal to solubilize the osteogenic protein at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml may be desirable. Amino acids having a net positive charge (e.g. net 1+ species such as arginine, histidine, lysine and the ethyl esters of glycine and beta-alanine), preferably a net 2+ charge (e.g. the ethyl ester of histidine, the methyl esters of lysine and arginine, and agmatine), are useful in this regard. Amino acids having a net zero charge are useful in this regard provided that the positive charge of the compound is sufficiently distant (at least 2–3 $CH_2$ units away) from the neutralizing negative charge (e.g. net neutral species such as gamma-amino butyric acid, beta-amino propionic acid, and glycine-glycine dipeptide). Other solubilizing agents useful herein include poly(sorbate), dextran sulfate, guanidine, heparin, sodium chloride, glutamic acid hydrochloride, acetic acid and succinic acid. For use in solubilizing dimeric BMP, such as BMP-2, 3, 4, 5, 6, 7, 8, 9 and 10 and heterodimers of BMPs such as BMP-2/6 and BMP-2/7, preferred solubilizing agents include arginine and histidine (including esters thereof) and glutamic acid hydrochloride.

Glutamic acid hydrochloride (HCl) is the preferred solubilizing agent. It is used in concentrations of about 1 to about 20 mM (about 0.02 to about 0.37% w/v), preferably about 5 to about 10 mM (about 0.1 to about 1.8% w/v), and at a pH of less than about 6.0, preferably about 3.5 to about 5.25, preferably about 4.5. The composition also includes about 0.1 to about 5.0% (w/v), preferably about 0.5 to about 2.5%, of a sugar; most preferably about 0.5% sucrose; and about 0.5 to about 10.0% (w/v) glycine, preferably about 2.0 to about 2.5%. In order to prevent the formation of particulates, the glutamic acid hydrochloride composition may optionally include about 0.01 to about 0.1% (w/v) of a non-ionic surfactant, such as a polyoxyester, for example polysorbate 80, polysorbate 20 or Pluronic F-68. The sucrose/glycine ratio can be varied to provide moisture content and bulk characteristics to the composition. Other components may be substituted in the compositions of the present invention. For example, in place of glutamic acid, a mono- acid with pKa close to 4.5 can be used, such as acetic acid. Di- acid like succinic acid can be used, but at a lower concentration (about 1 mM preferred, rather than about 5 mM). When glutamic acid hydrochloride is used, either glutamic acid/hydrochloride or mixtures of glutamic acid and HCl may be used. Glutamic acid hydrochloride may also be used in hydrated form, such as glutamic acid hydrochloride monohydrate. With minor modifications, glutamic acid or glutamates, for example sodium glutamate, may be used in place of glutamic acid hydrochloride. Glycine may be replaced in whole or in part by other amino acids with similar charge. In addition, other optional components may be added such as albumin, glycerol, mannitol and other sugars. Thus, the present invention includes compositions employing substituted components, as described above, for example, compositions using glutamic acid or sodium glutamate in place of glutamic acid hydrochloride. Other modifications will be apparent to those skilled in the art and are also encompassed by the present invention.

The above formulations may be lyophilized and reconstituted with water, providing for advantages in storage, shipping and stability. Lyophilized formulations of the present invention may comprise the following composition: about 3.12% to about 24.38% by weight BMP; about 0.52% to about 10.27%, preferably about 1.84% to 5.27% (w/w) glutamic acid hydrochloride; about 38.4% to about 75.7% by weight glycine; about 14.28% to about 47.15% by weight sucrose; and optionally about 0.15% to about 2.94% by weight polysorbate 80. For example, two preferred compositions of the lyophilized formulation are listed in Table 1 below:

TABLE 1

| a. 4.0 mg/ml formulation | |
|---|---|
| BMP-2 | 4.0 mg/ml (11.42% wt) |
| glutamic acid HCl | 0.918 mg/ml ( 2.62% wt) |
| glycine | 25 mg/ml (71.39% wt) |
| sucrose | 5 mg/ml (14.28% wt) |
| polysorbate 80 | 0.1 mg/ml ( 0.29% wt) |
| b. 2.0 mg/ml formulation | |
| BMP-2 | 2.0 mg/ml ( 6.06% wt) |
| glutamic acid HCl | 0.918 mg/ml ( 2.78% wt) |
| glycine | 25 mg/ml (75.72% wt) |
| sucrose | 5 mg/ml (15.14% wt) |
| polysorbate 80 | 0.1 mg/ml ( 0.30% wt) |

The above formulations can be reproducibly lyophilized in less than 40 hours, with moisture level well controlled. The formulations provide good storage stability at a variety of temperatures. The above formulations further provide higher solubility of BMP, providing support for administration of higher doses of BMP, and show good compatibility with the devices described above. With minor variations and modifications within the present invention, the above formulation may be used to prepare solutions of higher concentrations of at least about 4 mg/ml of BMP-2 or other BMPs.

Various well known methods may be used to compound the osteogenic protein and solubilizing agents for use herein, including but not limited to ultrafiltration, dialysis, gel filtration, and hydrophobic interaction chromatography.

The porous particulate polymer matrix component useful in the practice of the subject invention is a polymeric material that can be formed into porous particles as described below thereby providing in situ scaffolding for the osteogenic protein, while having biodegradable properties allowing for replacement by new bone growth. Examples are polymers of amino acids, orthoesters, anhydrides, propylene-co-fumarates, or a polymer of one or more α-hydroxy carboxylic acid monomers, (e.g. α-hydroxy acetic acid (glycolic acid) and/or α-hydroxy propionic acid (lactic acid)). The latter can be employed in its d- or l- form, or as a racemic mixture, the racemic mixture being preferred. When a copolymer of lactic acid and glycolic acid is employed (PLGA), the molar ratio of monomers can range from 1:99 to 99:1 depending upon the desired bioerosion lifetime which in turn depends upon the clinical indication being addressed, as more than 50% of either monomer gives longer bioerosion lifetime (slower biodegradation). The molecular weight of the polymer can range from about 1,000 to 100,000 (relative to polystyrene in $CHCl_3$) with 30,000-50,000 being preferred when a 50:50 copolymer is employed. In general, the higher the molecular weight, the slower the biodegradation.

The polymeric matrix component of the subject invention is used in the form of highly porous to hollow (with surface porosity) particles, hereinafter collectively referred to as "porous particles." These porous particles are generally spherical having diameters of 150 to 850 microns, preferably 150–500 microns, most preferably 150–300 microns. This particle size creates sufficient spacing between particles to allow mammalian osteoprogenitor cells to infiltrate and be positively influenced by (evidenced by an increase in osteogenic activity/bone growth rate) the osteogenic protein.

U.S. Pat. No. 5,171,579 discloses that the average surface area per porous particle is critical to optimize bone formation. Specifically, porous particles useful in bone formation according to the present invention should have an average surface area of from about 0.02 to 4 $m^2/g$. WO 93/06872 further discloses that it is possible to produce porous particles having the desired surface area by introducing a "porosigen" (composition capable of imparting porosity by increasing particle surface area) into the solution used to produce the porous particles. The disclosure of the above publications are hereby incorporated by reference. It is also possible to control the bioerosion rate by subjecting the porous particles to sterilizing doses of γ radiation. The higher the γ radiation dose, the faster the bioerosion. Particles useful herewith have a porosity such that the surface area of the particles is increased about 2–250 fold over the surface area of non-porous particles of comparable size.

A preferred method of production of the porous particles useful in the invention is, generally speaking, a solvent evaporation process comprising dissolving the polymer (in e.g. $CH_2Cl_2$), and adding a porosigen such as NaCl, mannitol or sucrose in solid and/or liquid form. When porosigen is added in solid form, the matrix-porosigen solution takes the form of a suspension.

Another preferred method of production of the porous particles useful in the invention is a solvent extraction method, wherein the porosigen is added in liquid form with concomitant homogenization. When porosigen is added in liquid form with homogenization, the matrix-porosigen solution takes the form of an emulsion. With either method, the matrix-porosigen emulsion is added to an excess aqueous solution containing surfactant such as poly(vinyl alcohol) with controlled stirring and temperature. The resultant porous particles are hardened by extracting or evaporating residual solvent, and dried. PLGA particles useful in the subject invention made utilizing 50% NaCl as a porosigen have a surface area of between about 0.2 and 0.6 $m^2/g$; and particles made using sucrose as a porosigen have a surface area of between about 0.04 and 0.09 $m^2/g$. PLGA particles useful in the present invention made using liquid porosigen with homogenization have a surface area of between about 0.02 and 4 $m^2/g$.

The porous nature of the particles useful in the present invention creates sufficient surface area for protein adsorption and increases biodegradation, the desirable extent of both being dependent upon the clinical indication being addressed. Surface area can be measured by any conventional technique. For example, BET surface area analysis can be employed using a Micromeritics ASAP 2000 system, which measures surface area based upon adsorption and desorption of Krypton gas at the surface and within the pores of the solid sample. The unit calculates and prints out the surface area:

$$\frac{1}{VA[(P_0/P) - 1]} = \frac{C-1}{V_mC}(P/P_0) + \frac{1}{V_mC}$$

V = volume absorb at pressure P
$P_0$ = saturation pressure
$P/P_0$ = relative pressure
P = pressure
C = constant
A = gas cross sectional area
Vm = Monolayer Capacity
  By plotting $$\frac{1}{VA((P_0/P) - 1}$$

vs $P/P_0$ the slope being $$\frac{C-1}{V_mC}$$

and the intercept being $$\frac{1}{V_mC},$$

the surface area $$S_t = \frac{V_mNA}{V}$$

where N = Avogadro's number and V = molar volume. The amount of porous particles used to treat a particular defect will, of course, depend upon the size of the defect being treated, and on the effective amount required to adsorb the osteogenic protein.

A protein-sequestering material useful in the practice of the subject invention is pharmaceutically acceptable human blood, preferably autogenous blood. When added to an osteogenic protein/porous particle mixture, the blood clots to form a malleable composite wherein the adsorbed protein is sequestered within the matrix for a time sufficient to allow the protein to increase the otherwise natural rate of osteogenic activity of the infiltrating mammalian progenitor cells. In the absence of such blood clot, osteogenic protein desorbs from the PLGA particles in situ at a rate such that the osteoinducing effect of the protein is not clinically significant. The ratio of blood to porous particles useful herein is 1:0.5 to 1:10 (v:v), preferably 1:5 (v:v), and more preferably 1:2 (v:v), which ratio represents the amount necessary to prevent desorption from the polymer matrix, yet not so much that the progenitor cells are prevented from infiltrating the matrix, thereby providing the protein the opportunity to assist the osteogenic activity of the progenitor cells. For each 1 ml defect, the amount of blood required will therefore generally be about 0.5–1.0 ml. In cases where large doses of osteogenic protein are employed, clot facilitating agents such as thrombin may be employed to offset the dilution effect of the osteogenic protein.

The compositions of the present invention may optionally include other protein-sequestering agents. These protein-sequestering agents are preferably osteogenic or osteoconductive. Suitable agents include cellulosic materials such as alkylcelluloses (including hydroxyalkylcelluloses), such as methylcellulose, ethylcellulose, hydroxyethylcellulose, hydroxypropylcellulose, hydroxypropyl-methylcellulose, and carboxymethylcellulose. Other sequestering agents include hyaluronic acid, alginates, such as sodium alginate or calcium alginate, poly(ethylene glycol), polyoxyethylene oxide, carboxyvinyl polymer, and poly(vinyl alcohol).

In a preferred embodiment of the present invention, the cellulosic protein sequestering agent above may be diluted using aqueous glycerol as the diluent. The preferred sequestering agents for this embodiment include carboxymethylcellulose. The cellutosic protein sequestering agent is preferably present in a concentration of about 2 to about 10% (w/v), preferably about 2.75 to 5.5%(w/v); aqueous glycerol is present in concentrations of about 20 to about 80% (v/v), preferably about 60 to 80% (v/v); and ratios (v/v) of sequestering agent liquid solution to porous micropolymer particles are from about 0.1 to about 0.9, preferably about 0.2 to 0.5.

To improve the osteoconduction of the formulation and retention of the formulation at the wound site, to reduce formulation setup time and improve handling characteristics, a calcium sulfate hemihydrate-containing substance (CSHS) is added to the formulation. In addition to improved moldability and handling of the device, addition of the CSHS decreased the preparation time required for the device. It also allows preparation of devices with good handling and molding properties in patients with poor or slow blood clotting. Preferred CSHS include pure calcium sulfate hemihydrate, also known as Plaster of Paris and a 35:65 mixture of Plaster of Paris and hydroxyapatite. Addition of at least about 0.2 to 2.0 g, preferably at least about 0.8 to 2.0 g of the CSHS per 2 mL of porous particles in a rhBMP-2/blood clot/BEP device is desirable.

In another embodiment of the present invention, the formulation comprises osteogenic protein, autogenous blood and a calcium sulfate hemihydrate-containing substance (CSHS), without porous polymeric particles. Preferred compositions of such formulations comprise the components in relative amounts of about 0.5 mL osteogenic protein, to about 5.5 mL autogenous blood and about 1 to 10 g CSHS. In this embodiment, the CSHS provides a structural matrix function, an osteoconductive matrix, and a protein sequestering function, in addition to that of the autogenous blood. The optimal formulation is determined by addition of varying quantities of CSHS in 1 g increments to the blood and osteogenic protein mixture. The devices are observed immediately following preparation and 1 to 2 hours following preparation. The quantity of CSHS which provides the best handling properties both immediately after and 1 to 2 hours after preparation will be optimal.

In yet another embodiment of the present invention, the formulation comprises suitable mixtures of osteogenic protein and calcium sulfate hemihydrate-containing substance. Preferred compositions of such formulations comprise approximately 0.5 to 2 grams, preferably 1 gm, of osteogenic protein per approximately 10 to 20 grams, preferably 12 grams of CSHS in approximately 3 ml of $H_2O$. For example, the osteogenic protein can be delivered using 0.5 ml of a 2 mg/ml BMP-2 solution, or 0.25 ml of a 4 mg/ml BMP-2 solution. In this embodiment, the CSHS provides a structural matrix function, an osteoconductive matrix, and a protein sequestering function.

The above formulations may optionally include a protein-sequestering agent, such as described above. Additional optional components useful in the practice of the subject application include, e.g. cryogenic protectors such as mannitol, sucrose, lactose, glucose, or glycine (to protect the formulation from degradation during lyophilization), antimicrobial preservatives such as methyl and propyl parabens and benzyl alcohol, antioxidants such as EDTA, citrate, and BHT (butylated hydroxytoluene), and surfactants such as poly(sorbates) and poly(oxyethylenes), etc. Of course, the traditional preparation of formulations in pharmaceutically acceptable form (i.e. pyrogen free, appropriate pH and isotonicity, sterility, etc.) is well within the skill in the art and is applicable to the formulations of the subject invention.

The osteogenic protein and porous particles of the formulations may be provided to the clinic as a single vial formulation, either as a solution or in lyophilized form, or the formulation may be provided as a multi-component kit wherein, e.g. the osteogenic protein is provided in one vial and the porous particles and calcium sulfate hemihydrate-containing substance each are provided in separate vials. The blood to be used in the formulation is admixed at a time prior to use sufficient to allow clotting, generally 15 to 180 minutes prior to use, taking into account the well-known patient-to-patient variability in clotting time, as well as the ability of CSHS to accelerate formability of the device.

The formulations of the subject invention provide malleable implants that allow therapeutically effective amounts of osteoinductive protein to be delivered to an injury site where cartilage and/or bone formation is desired. Such an implant may be used as a substitute for autologous bone graft in fresh and non-union fractures, spinal fusions, and bone defect repair in the orthopaedic field; in cranio/maxillofacial reconstructions; for prosthesis integration, especially as a surface coating to improve fixation of prosthetic implants such as hydroxylapatite coated prostheses; in osteomyelitis for bone regeneration; and in the dental field for augmentation of the alveolar ridge and periodontal defects and tooth extraction sockets. When used to treat osteomyelitis or for bone repair with minimal infection, the osteogenic protein may be used in combination with porous microparticles and antibiotics, with the addition of protein sequestering agents such as alginate, cellulosics, especially carboxymethylcellulose, diluted using aqueous glycerol. The antibiotic is selected for its ability to decrease infection while having minimal adverse effects on bone formation. Preferred antibiotics for use in the devices of the present invention include vancomycin and gentamycin. The antibiotic may be in any pharmaceutically acceptable form, such as vancomycin HCl or gentamycin sulfate. The antibiotic is preferably present in a concentration of from about 0.1 mg/mL to about 10.0 mg/mL.

The lower viscosity formulations may also be used as a percutaneous injection to accelerate healing of closed fractures. In certain of these uses, the compositions of the subject invention may be used in combination with various bone cements, including erodible bone cements such as poly(propylene-co-fumarate) and certain hydroxyapatite cements. Also, certain of these uses will utilize bioerodible hardware such as erodible plates, screws, etc. As alluded to above, the dosage regimen will be determined by the clinical indication being addressed, as well as by various patient variables (e.g. weight, age, sex) and clinical presentation (e.g. extent of injury, site of injury, etc.). In general, the dosage of osteogenic protein will be in the range of from about 10 to 1000 µg, preferably from about 10 to 100 µg.

The following examples are illustrative of the present invention and are not limiting in any manner. Modifications, variations and minor enhancements are contemplated and are within the present invention.

EXAMPLE 1

FORMULATION OF BMP USING GLUTAMIC ACID HCL

Recombinantly produced BMP-2 is solubilized (2 mg/ml) in a composition of 2.5% (w/v) glycine, 0.5% (w/v) sucrose, 0.01% (w/v) polysorbate 80 and 5 mM (about 0.092% w/v) glutamic acid HCl at pH=4.5.

EXAMPLE 2

SOLUBILITY AND STABILITY OF BMP FORMULATIONS USING GLUTAMIC ACID HCL AS SOLUBIZING AGENT

The above compositions of Example 1 are lyophilized and stored at −80°, 4°, 30° and 40° C. The lyophilized samples are inspected for appearance prior to reconstitution. All appeared as good white cakes and did not change with time or temperature.

The compositions are reconstituted at 2 weeks, 1 month, 3 months and 4.5 months after lyophilization and studied for reconstitution time, particulate formation, pH after reconstitution, % moisture content, concentration of BMP-2 after reconstitution, % aggregate formation and specific activity in the W-20 bioassay for BMP activity.

The above compositions reconstituted within about 10–30 seconds, even after 4.5 months storage. Upon reconstitution, the compositions show no visible particulates, little or no change in moisture content, little or no loss of protein, low levels of aggregates, and are active in the W20 bioassay.

EXAMPLE 3

CALCIUM SULFATE HEMIHYDRATE-CONTAINING DEVICE 0.8, 1.2, 1.6 and 2.0 g of either calcium sulfate hemihydrate (Calset ®, Lifecore Biomedical) or 35:65 mixture of calcium sulfate hemihydrate:hydroxyapatite (Hapset ®, Lifecore Biomedical) are added to 2 mL of the rhBMP-2/autogenous blood/porous microparticle mixture. The preparations are observed for consistency at the time of preparation and evaluated on a ten-point scoring scale (score of 5 is optimal) for handling characteristics fifteen minutes after preparation. Table 2 shows the results of this evaluation. Because only 2 mL of mixture was used, the formulations tended to dry more quickly than the 10 mL size used for actual implants.

TABLE 2

| Amount CSHS added grams | Plaster of Pairs | | 35:65 Plaster of Paris:hydroxyapatate | |
|---|---|---|---|---|
| | Consistency at time of preparation | Handling at 15 mins | Consistency at time of preparation | Handling at 15 mins |
| 0.0 | 1 | 4 | 1 | 4 |
| 0.8 | 1 | 5 | 6 | 6 |
| 1.2 | 1 | 3 | 4 | 6 |
| 1.6 | 2 | 5 | 4 | 6 |
| 2.0 | 3 | 5 | 5 | 7 |

Key:
0 = Liquid (like water).
1 = Device flows; cannot be molded and segmented.
2 = Device just flows; cannot be molded and segmented.
3 = Device does not flow; device molding and segmenting suboptimal; molded device is limp.
4 = Device does not flow; device molding and segmenting suboptimal; molded device is soft.
5 = Unified device formation; device is shapable and remoldable; molded device is malleable.
6 = Unified device formation; device molding and segmenting suboptimal; molded device is brittle, but segmented pieces are cohesive.
7 = Unified device formation; device molding and segmenting suboptimal; molded device is brittle and segmented pieces are non-cohesive.
8 = No unified device formation; device cannot be segmented and molded; large aggregates.
9 = No unified device formation; device cannot be segmented and molded; small aggregates.
10 = No unified device formation; device cannot be segmented and molded; powder.

EXAMPLE 4

PREPARATION OF IMPLANT USING CALCIUM SULFATE HEMIHYDRATE-CONTAINING SUBSTANCE

A 50:50 random copolymer of lactic acid and glycolic acid (PLGA) having an average molecular weight of 30–40 kD, a number average molecular weight of about 20 kD (by gel permeation chromatography relative to polystyrene standards) and an inherent viscosity of 0.35–0.45 dL/g was dissolved in $CH_2Cl_2$ (15(w/v), and 10 g porosigen (7.5% w/v) was suspended in this solution. The resulting solution was added to an excess poly(vinyl alcohol) aqueous solution (0.1% w/v). After a few hours of stirring under partial vacuum (24 inches Hg), the particles were hardened in excess cold ethanol (95%). The resulting particles were washed with water for injection and vacuum dried to give a free-flowing product. BET surface area analysis was performed using a Micrometrics ASAP 2000 system as described above, and the particles had a surface area of between about 0.2 and 1.0 $m^2/g$: particles made using sucrose as a porosigen had a surface area of between about 0.04 and 0.09 $m^2/g$. The porous particles are sterilized by γ irradiation prior to use. For each implant intended for human use, 10 ml of porous particles are placed in a sterile cup. The desired amount (4–10 g) of calcium sulfate hemihydrate-containing substance is added to the porous particles in the sterile cup and the cup is shaken to mix.

Lyophilized recombinant human BMP-2 (rhBMP-2) (2 mg in buffer) is reconstituted with 1 ml sterile water for injection (WFI). 0.5 ml of the rhBMP-2 solution (1 mg) is drawn into a 3 ml syringe using a 22 g needle, which is then removed.

5.5 ml of the patient's venous blood is drawn into a 10 ml syringe (not through a heparinized line), the needle of which is removed. The blood is expressed evenly over the porous particles/calcium sulfate mixture in the cup. The rhBMP-2 solution is added to the components in the sterile cup. If necessary, the entire mixture is gently stirred with a stainless steel spatula to achieve uniform consistency. The cup is covered and allowed to sit at room temperature for about 15 minutes. The implant mixture should be used within the following two hours.

When the desired consistency of the malleable implant is obtained, the bony defect is exposed by surgical incision at the site of injury. The implant is applied by the surgeon by shaping the malleable composite of porous particles/CSHS/rhBMP-2/blood clot to span the bony defect which is desired to be treated. The incision is then closed using conventional methods. Healing is monitored by X-ray analysis of the defect site.

EXAMPLE 5

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of formulations of BMPs with the activity of known BMPs are described.

B. W-20 Alkaline Phosphatase Assay Protocol

W-20 cells are plated into 96 well tissue culture plates at a density of 10,000 cells per well in 200 µl of media (DME with 10% heat inactivated fetal calf serum, 2 mM glutamine and 100 Units/ml penicillin + 100 µg/ml streptomycin. The cells are allowed to attach overnight in a 95% air, 5% $CO_2$ incubator at 37° C.

The 200 µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 µl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 µl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table 3.

TABLE 3

| Absorbance Values for Known Standards of P-Nitrophenol Phosphate | |
|---|---|
| P-nitrophenol phosphate umoles | Mean absorbance (405 nm) |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to µmoles of p-nitrophenol phosphate cleaved per unit time as shown in Table 4.

TABLE 4

| Alkaline Phosphatase Values for W-20 Cells Treating with BMP-2 | | |
|---|---|---|
| BMP-2 concentration ng/ml | Absorbance Reading 405 nmeters | umoles substrate per hour |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of new BMP formulations to known active BMP formulations.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 μl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

EXAMPLE 6

IMPLANTATION OF DEVICE INCLUDING ANTIBIOTIC 0.55 g of dry carboxymethyulcellulose (CMC) powder is added to 20 mL of glycerol/$H_2O$ (75:25 v/v) (or 60:40 v/v) with the amounts of vancomycin HCl or gentamycin sulfate antibiotic specified in Table 5.

10 uL of 8 mg/mL rhBMP-2 formulation (in buffer as described for the 2.0 mg/ml formulation at pages 6–7 above) or 10 uL of control (buffer without BMP-2) is added to a sterile eppendorf tube containing 37.2 mg (0.200 mL) 50:50 PLGA porous particles.

110 uL of the CMC/antibiotic/glycerol/$H_2O$ mixture is dispersed over the porous particles/rhBMP-2 mixture. The mixture is stirred until a homogenous mixture is formed. The result is a 200 uL device containing 40 ug/100 uL rhBMP-2. A device is then implanted subcutaneously in each of 50 rats divided into 10 groups for assay in the rat ectopic study described in Example 7 below.

TABLE 5

| Test Group | | Average Bone Score |
|---|---|---|
| Negative control | (no B MP) | 0 |
| Positive control | BMP(10 ug/100 uL) | 2.75 |
| Vmycin 10.0 mg/100 uL | BMP(40 ug/100 uL) | 4 |
| Vmycin 5.0 mg/100 uL | BMP(40 ug/100 uL) | 4.8 |
| Vmycin 1.0 mg/100 uL | BMP(40 ug/100 uL) | 3.5 |
| Vmycin 0.1 mg/100 uL | BMP(40 ug/100 uL) | 4.2 |
| Gmycin 10.0 mg/100 uL | BMP(40 ug/100 uL) | 3.4 |
| Gmycin 5.0 mg/100 uL | BMP(40 ug/100 uL) | 3.1 |
| Gmycin 1.0 mg/100 uL | BMP(40 ug/100 uL) | 4.1 |
| Gmycin 0.1 mg/100 uL | BMP(40 ug/100 uL) | 3.8 |

Bone Histology Scoring Code:
0 = No bone
1 = Bone in 10–20% of section
2 = Bone in 20–40% of section
3 = Bone in 40–60% of section
4 = Bone in 60–80% of section
5 = Bone in 80–100% of section
Controls contained no antibiotic
Vmycin = vancomycin HCl
Gmycin = gentamycin sulfate
BMP = recombinant human BMP-2

EXAMPLE 7

The effectiveness of the devices of the present invention may be evaluated in the following assays:

CANINE CALVARIAL DEFECT IMPLANT ANALYSIS

Two male and two female dogs are placed under general anaesthesia and four trephine holes of approximately 12 mm each are made in each skull using an Acra-cut DG II cranial drill. All holes are filled with an implant consisting of rhBMP-2, PLGA porous particles, calcium sulfate-hemihydrate containing substance, and autologous blood which has been allowed to clot to form a moldable implant. The dose of rhBMP-2 is approximately 200 μg/ml in each implant. One male and one female animal is sacrificed at 4 weeks and the remaining animals are sacrificed at 8 weeks after surgery.

After sacrifice, the left rostral and right caudal calvarial sites of each animal are used for biomechanical testing, and the right rostral and left caudal calvarial sites are used for histopathology.

RAT ECTOPIC STUDY

Twenty four Long-Evans male rats are divided into 6 test groups. Each receives a subcutaneous implant, 200 uL in size, with either a 0 or 20 ug/100 uL dose of rhBMP-2/PLGA porous particles/blood clot and either no calcium sulfate hemihydrate additive; 200 mg Calset (POP); or 200 mg Hapset (35:65 POP:HA).

After 14 days, the rats are sacrificed and each animal is evaluated for bone formation.

RAT FEMORAL DEFECT IMPLANT ANALYSIS

A critical-size defect (5 mm) is surgically created in the mid-diaphysis of the left femur of each of 56 male Long Evans retired breeder rats (450–550 grams), by affixing a pre-drilled polyethylene plate to the anterior portion of the femur and excising a segment of bone with a carbide dental drill. A bioerodible implant is prepared by mixing rhBMP-2 (in varying amounts), PLGA porous paticles, calcium sulfate hemihydrate-containing substance and venous rat blood and allowing the blood to clot to form a moldable implant. Eight groups of seven animals each are implanted as follows: 0 μg rhBMP-2; 0.93 μg rhBMP-2; 3.1 μg rhBMP-2; and 9.3 μg rhBMP-2.

Animals are radiographed at Day 0 and Weeks 3, 6, and 9. The animals are sacrificed at week 9, the tissues surrounding the polyethylene plates are removed for histological examination, and the implanted and contralateral non-implanted femurs are harvested. Two femurs in each group are histologically examined, and the remaining femurs are used for biomechanical testing.

What is claimed is:

1. A composition comprising an osteogenic protein, about 0.1 to about 5.0% (w/v) of a sugar, about 1.0 to about 10.0% (w/v) glycine, and about 1 to about 20 mM of glutamic acid hydrochloride, wherein such composition has a pH of about 4.5.

2. The composition of claim 1, further comprising about 0.01 to about 0.1% (w/v) of a non-ionic surfactant.

3. A composition comprising an osteogenic protein, about 1 to about 10% (w/v) glycine, about 0.1 to about 5.0% (w/v) sucrose, about 0.01 to about 0.1% (w/v) non-ionic surfactant and about 5 to about 10 mM glutamic acid hydrochloride, wherein such composition has a pH less than about 6.0.

4. A composition comprising an osteogenic protein, about 2.5% (w/v) glycine, about 0.5% (w/v) sucrose, about 5 mM glutamic acid hydrochloride, and about 0.01% (w/v) polysorbate 80, wherein such composition has a pH of about 4.5.

5. A composition comprising a lyophilized formulation of about 3.12% to about 24.38% (w/w) BMP; about 0.52% to about 10.27% (w/w) glutamic acid hydrochloride; about 38.4% to about 75.7% (w/w) glycine; about 14.28% to about 47.15% (w/w) sucrose; and optionally about 0.15% to about 2.94% (w/w) polysorbate 80.

6. A composition according to claim 5 wherein the lyophilized formulation comprises relative weight amounts of about 4.0 mg/ml of BMP-2; about 0.918 mg/ml of glutamic acid hydrochloride; about 25 mg/ml of glycine; about 5 mg/ml of sucrose; and optionally about 0.1 mg/ml of polysorbate 80.

7. A composition according to claim 5 wherein the lyophilized formulation comprises relative weight amounts of about 2.0 mg/ml of BMP-2; about 0.918 mg/ml of glutamic acid hydrochloride; about 25 mg/ml of glycine; about 5 mg/ml of sucrose; and optionally about 0.1 mg/ml of polysorbate 80.

* * * * *

UNITED STATES PATENT AND TRADEMARK OFFICE
CERTIFICATE OF CORRECTION

PATENT NO. : 5,385,887
DATED : January 31, 1995
INVENTOR(S) : Yim et al.

It is certified that error appears in the above-identified patent and that said Letters Patent is hereby corrected as shown below:

At column 1, line 31, please change "oppermann" to -- Oppermann --.

At column 10, line 54, please change "(15(w/v)" to -- (15% w/v) --.

Signed and Sealed this

Twenty-ninth Day of August, 1995

Attest:

BRUCE LEHMAN

Attesting Officer     Commissioner of Patents and Trademarks